United States Patent
Lamb

(10) Patent No.: US 9,616,066 B2
(45) Date of Patent: Apr. 11, 2017

(54) THERAPY FOR CONSTIPATION

(71) Applicant: G. Blair Lamb, Kilbride (CA)

(72) Inventor: G. Blair Lamb, Kilbride (CA)

(73) Assignee: 2294719 Ontario Limited, Milton, Ontario (CA)

(*) Notice: Subject to any disclaimer, the term of this patent is extended or adjusted under 35 U.S.C. 154(b) by 0 days.

(21) Appl. No.: 14/700,795

(22) Filed: Apr. 30, 2015

(65) Prior Publication Data

US 2015/0231139 A1    Aug. 20, 2015
US 2017/0065599 A9    Mar. 9, 2017

Related U.S. Application Data

(63) Continuation-in-part of application No. PCT/CA2013/050829, filed on Oct. 31, 2013, which is a continuation of application No. 13/664,762, filed on Oct. 31, 2012, now abandoned.

(51) Int. Cl.
     *A61K 31/536*    (2006.01)
     *A61K 31/365*    (2006.01)
     *A61K 45/06*    (2006.01)

(52) U.S. Cl.
     CPC .......... *A61K 31/536* (2013.01); *A61K 31/365* (2013.01); *A61K 45/06* (2013.01)

(58) Field of Classification Search
     USPC ........................................................ 424/727
     See application file for complete search history.

(56) References Cited

U.S. PATENT DOCUMENTS

| | | | |
|---|---|---|---|
| 6,476,078 B1 * | 11/2002 | Jerussi | A61K 45/06 514/262.1 |
| 6,534,539 B2 * | 3/2003 | Feinle | A61K 31/00 514/449 |
| 6,734,314 B2 | 5/2004 | Keri et al. | |
| 6,982,283 B2 | 1/2006 | Ueno | |
| 7,862,840 B2 | 1/2011 | Eidenberger | |
| 8,278,323 B2 | 10/2012 | Dolle et al. | |
| 2004/0096527 A1 | 5/2004 | Jang | |
| 2005/0196374 A1 | 9/2005 | Ueda | |
| 2006/0177438 A1 | 8/2006 | Kopin et al. | |

FOREIGN PATENT DOCUMENTS

JP    2009057365    3/2009

OTHER PUBLICATIONS

Bryson et al. British Journal of Clinical Pharmacology (2009) 67:3, pp. 309-315.*
Guarino, A. Pain Medication (Malden, Mass.), (2005), vol. 6(4), pp. 327-328.*
Guarino, A. Pain Medication (Malden, Mass.), (2005), vol. 5(4), pp. 327-328.
Bazzocchi (Gastroenterology (2001), vol. 120, No. 5 supplement 1, pp. A-752).

* cited by examiner

*Primary Examiner* — Nyeemah A Grazier
(74) *Attorney, Agent, or Firm* — Susan Tandan; Gowling WLG (Canada) LLP

(57) ABSTRACT

A method is disclosed of treating acute, sub-acute or chronic constipation in a patient having a condition requiring such treatment. The method includes administering a lipase inhibitor. Also provided is a method of treating chronic pain in a patient which includes administration of a lipase inhibitor, with or without pain medication.

4 Claims, No Drawings

THERAPY FOR CONSTIPATION

CROSS-REFERENCE TO RELATED APPLICATIONS

The present application is a continuation-in-part of PCT application PCT/CA2013/050829, filed Oct. 31, 2013, and designating the United States. PCT/CA2013/050829 receives the benefit of U.S. patent application Ser. No. 13/664,762, filed Oct. 31, 2012, now abandoned. The contents of each of the above applications are incorporated herein in their entirety by reference.

FIELD OF THE INVENTION

The present invention relates to methods and compositions for the treatment of bowel disorders, especially chronic pain and constipation associated with the administration of drugs, for example, painkillers such as opioids, and other medications.

BACKGROUND OF THE INVENTION

Constipation is a frequent side effect of many conditions and medications. For example, opioids may lead to constipation since these agents decrease peristaltic activity in the gastrointestinal (GI) tract. Because of the mechanisms involved in opioid-induced constipation, some treatments that may be applicable for common, functional constipation are inappropriate for ambulatory-care patients prescribed opioid analgesics. Also in these patients, the distress of constipation may add to the discomfort already present from pain, and they may decrease or discontinue the opioid to avoid constipation. Therefore, motivating such patients to comply with their opioid therapy also requires an approach for managing constipation.

Constipation is broadly defined as the passage of hard, dry stools less frequently than the patient's usual bowel-habit pattern.

Constipation resulting from opioid use is the most common component of a more general condition called opioid-induced bowel dysfunction, OBD. Signs and symptoms of OBD include dry hard stools, straining during evacuation, incomplete evacuation, bloating, abdominal distension, and retention of the contents of the bowel.

Bulk-forming laxatives are typically not appropriate in opioid-induced constipation because peristalsis is inhibited in these patients so stool softener and bowel stimulants are often used. Some patients may take mild over-the-counter bulk laxatives and fail to mention this to their physician. This can result in painful, colic-like symptoms.

Attempts have been made to solve the problem of opioid-induced constipation. For example, U.S. Pat. No. 6,982,283 discloses a method for treating drug-induced constipation that comprises administering an effective amount of 15-keto-prostaglandin compound to a subject suffering from drug-induced constipation or a subject having a strong possibility of suffering from it. U.S. Pat. No. 8,278,323 describes certain quinolizidine and octahydropyridopyrazine compounds, pharmaceutical compositions, and methods of their use as opioid receptor antagonists for the treatment of opioid-induced constipation. The use of an opioid antagonist effectively reduces the amount of physiologically available opioid. However, the dose that leads to constipation is approximately four-fold less than the dose required for an analgesic response.

Accordingly, it is desirable to develop a novel method of treating constipation, including drug-induced constipation.

SUMMARY OF THE INVENTION

In one aspect of the invention, there is provided a method of treating acute, sub-acute or chronic constipation in a patient having a condition requiring such treatment, comprising the administration of a lipase inhibitor.

In one preferred embodiment, the lipase inhibitor is selected from the group consisting of: orlistat, atl-962 (cetilistat) and gt389-255.

In another preferred embodiment, the lipase is naturally occurring and may include, for example saponins, platycodin saponins, scabio saponins, sessiloside and chiisanoside, chikusetsusaponins, dioscin and derivatives, escins, teasaponins, cyclocariosides, polyphenols, oolong tea polyphenols, polyphenol-rich extracts including grape seed extract, *nelumbo nucifera* extract, *salacia reticulata* hot water extract, peanut shell extract, *mangifera indica* leaf and steam bark extracts, ct-ii extracts, terpenes including carnosic acid, crocin and crocetin and pancreatic lipase inhibitors from microbial sources such as lipstatin.

In another embodiment, the condition is selected from the group consisting of drug-induced constipation, including opioid administration, e.g. opioid-induced bowel dysfunction (OBD), dehydration, lazy bowel, paralytic bowel, menstruation related constipation, bowel resection and being bedridden.

In a further embodiment, the lipase inhibitor is administered topically, intramuscularly (IM), intravenously (IV), subcutaneously (SC), or mucosally.

In yet another embodiment, the preferred lipase inhibitor is orlistat or cetilistat.

In another aspect, the invention is a method for treating chronic pain comprising administering a pain medication in combination with a lipase inhibitor.

In another aspect, of the invention there is provided a composition for the treatment of chronic constipation comprising 30 to 150 mg of a lipase inhibitor, preferably 60-120 mg, and optionally comprising another medication, such as a pain medication.

In a preferred embodiment, the composition is formulated for oral administration.

In another embodiment, the composition is in the form of a tablet, lozenge, pill, troche, capsule, soft-gel capsule, sachet or other combining vehicle, elixir, powder, including lyophilised powder, solution, granule, suspension, emulsion, syrup or tincture. Slow-release, or delayed-release, forms may also be prepared, for example, in the form of coated particles, multi-layer tablets or microgranules.

In another embodiment, the composition is provided in a compliance-enhancing blister pack.

DETAILED DESCRIPTION

The present invention provides a novel method of treatment for constipation. This novel type of treatment has a much improved therapeutic result for those who are suffering chronic constipation related to the use of drugs such as pain medications, e.g. opiates, other pain-killers, antidepressants and other situations such as paralysis, infection, cancer, radiation therapy and dehydration.

Lipase inhibitors are typically used for aiding weight loss. The active ingredient in some of the prescription products such as Xenical™ and Alli™ is orlistat. Other lipase inhibitors that function in the same way are herbal or are naturally sourced.

Lipase inhibitors block the action of the two compounds found in the digestive juices of the stomach and small intestine. These enzymes are known to break down the fat molecules that are in our diet. Without the action of these compounds, the molecules of fat are too large to be digested by our stomach and then to enter our bloodstream. Lipase inhibitors essentially keep the fat molecule intact and undigested, and thus, instead of becoming part of the body, the fat is excreted as waste through the bowels.

One of the known side effects of lipase inhibitors like Xenical™ is that the patient may experience loose bowels including episodes of diarrhea. This is, of course, a negative side effect for those persons who are taking the medication for weight-loss.

For those persons facing a problem of chronic constipation, including patients who are not overweight, and/or patients not seeking treatment for weight-loss (e.g. a patient having a normal body mass index (BMI), e.g. a BMI of less than 25), the use of lipase inhibitors offers a new treatment alternative. The use of lipase inhibitors that block the production of pancreatic and gastric enzymes and inhibit the breakdown of fats is herein provided to treat chronic constipation which is a novel use for these compounds.

According to the present invention, synthetic, chemical or naturally-derived lipase inhibitors can be used to relieve chronic constipation for persons who are using medications that induce constipation, including pain medications such as opiates or other painkillers, and other constipating drug treatments such as anti-depressants, and the like.

To treat constipation, the lipase inhibitor may be administered to a patient simultaneously with a second, third or more medications being used by the patient, either separately, i.e. in distinct dosage forms, or admixed with the other medications to form a single composition. In either case, a selected dosage of the other medication, e.g. a pain medication, is administered to a patient with a treatment dosage of lipase inhibitor (e.g. 30-150 mg). In one embodiment, the selected dosage of a pain medication, such as an opioid, may be a full treatment dosage (e.g. 60-120 mg morphine), or may be a series of partial treatment dosages that equal to a full treatment dosage (e.g. 3×20 mg=60 mg daily, or 3×40 mg=120 mg daily). The treatment dosage may be a daily dosage, or a dosage given 2 or more times daily, such as 1-4 times daily. A composition comprising a lipase inhibitor combined with a pain medication, particularly an opioid pain medication, advantageously prevents abuse by a patient of a pain medication, due to the dual effect of the composition to treat both pain and constipation. Administration of an excess of such a composition will result in an undesirable purgative effect.

A method for treating chronic pain is also provided comprising administering to a patient in need of treatment, a lipase inhibitor, optionally in combination with a pain medication. Chronic pain, such as abdominal and back pain, resulting from any condition may be treated using the present method. Examples of conditions leading to chronic pain include, but are not limited to, fibromyalgia, irritable bowel syndrome, including inflammatory bowel disease, characterized by chronic abdominal pain, discomfort, bloating, and alteration of bowel habits (e.g. diarrhea and/or constipation), and the like.

Some examples of lipase Inhibitors that may be used in the methods of the present invention include orlistat which is a pancreatic lipase, atl-962 (also known as cetilistat) which is another pancreatic lipase and gt389-255 which is another lipase inhibitor.

In addition, according to the invention, naturally-sourced lipase inhibitors may be used. These include plant-derived lipase inhibitors such as, but not limited to, saponins, platycodin saponins, scabio saponins, sessiloside, chiisanoside, chikusetsusaponins, dioscin and derivatives, escins, teasaponins and cyclocarios. The use of polyphenols, such as oolong tea polyphenols, are included within the scope of the invention. Also included are polyphenol-rich extracts such as grape seed extract, *nelumbo nucifera* extract, *salacia reticulata* hot water extract, peanut shell extract, *mangifera indica* leaf and steam bark extracts and ct-II extracts.

Furthermore, terpenes such as carnosic acid, crocin and crocetin, may also be used in the present invention. Pancreatic lipase inhibitors from microbial sources such as lipstatin may also be used.

To treat chronic pain, the lipase inhibitor may be administered to a patient at dosages of about 30 to 150 mg, preferably 60-120 mg, up to 4 times a day as needed, preferably, 1-3 times daily or less, e.g. 1-2 times per day.

The optional pain medication used to treat chronic pain according to the invention may be an opioid, e.g. morphine, codeine, thebaine, or derived therefrom, including, for example, hydrocodone, hydromorphone, oxycodone, and oxymorphone, or a non-opioid pain medication such as acetoaminophen and nonsteroidal anti-inflammatory drugs (e.g., ASA, ibuprofen, naproxen, diclofenac, celecoxib).

The pain medication may be administered to a patient simultaneously with the lipase inhibitor either separately, i.e. in distinct dosage forms, or admixed with the lipase inhibitor to form a single composition. In either case, a selected dosage of pain medication is administered to a patient with a treatment dosage of lipase inhibitor (e.g. 30-150 mg). The selected dosage of pain medication may be a full treatment dosage (e.g. 60-120 mg oxycodone), or may be a series of partial treatment dosages that equal to a full treatment dosage (e.g. 3×20 mg=60 mg daily, or 3×40 mg=120 mg daily). The treatment dosage may be a daily dosage, or a dosage given 2 or more times daily, such as 1-4 times daily.

In the present invention, various modes of administration may be used. Depending on the formulation, the lipase inhibitor may be administered topically, IM, IV, IM, and via mucosal routes.

Compositions of the invention may be prepared by means known in the art for the preparation of pharmaceutical compositions including blending, grinding, homogenizing, suspending, dissolving, emulsifying, dispersing and, where appropriate, mixing of the constipation-inducing medication, e.g. pain medication or other medication, with a lipase inhibitor(s), optionally together with one or more selected excipients, diluents, carriers and adjuvants.

The pharmaceutical composition of the invention may be in the form of a tablet, lozenge, pill, troche, capsule, soft-gel capsule, sachet or other combining vehicle, elixir, powder, including lyophilised powder, solution, granule, suspension, emulsion, syrup or tincture. Slow-release, or delayed-release, forms may also be prepared, for example in the form of coated particles, multi-layer tablets or microgranules. The composition may also be presented in a compliance-enhancing blister pack.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for the purpose of limitation.

Example 1

A 35-year-old female with fibromyalgia presented with chronic pain which is global pain disorder affecting much of her body. She was not overweight. She was prescribed opiate medication in the form of MS Contin™ (60 mg twice a day—BID) for pain management. Since beginning the MS Contin, she suffered from severe constipation. She would often go 7 to 10 days without a bowel movement. She would suffer abdominal discomfort, bloating, and sometimes require manual disempaction due to the severity of her constipation. The patient was given Colace™, Sennekot™, and bowel stimulants to attempt to correct her chronic constipation related to the pain medication. It was only partially and intermittently successful. She was then given the recommended doses of orlistat (120 mg twice per day orally—BID) with food, and noticed an improvement within 24 hours. Within one week, she had noticed that she had daily bowel movements. She took this new medication for one year and had good well-formed bowel movements most days. She reported no major side effects. This new treatment was seen as a complete success by both the patient and her doctor. She continues the opiate pain management and the orlistat with continued success for treatment of fibromyalgia. This illustrates that the lipase inhibitor improves opiate-related constipation.

Example 2

A 57-year-old female with fibromyalgia being treated with the tricyclic antidepressant, amitriptyline, suffered from a global pain disorder requiring pain management. She was of average weight, not over-weight. She was treated with amitriptyline that is a known therapeutic agent for mild to moderate fibromyalgia. This tricyclic antidepressant is also known for causing dry mouth, blurry vision and constipation. She had tried Colace and Sennekot (senna) with minimal benefit. The patient was given the recommended dosage of cetilistat (60 mg orally once per day with food) for her chronic constipation and within 24 hours, she had a bowel movement. She continued the cetilistat daily at one pill per day and was able to acquire regular bowel movements daily. She continued the medication for a year, e.g. amitriptyline and cetilistat, and continues to have good success with treatment of fibromyalgia and daily bowel movements. She reported no major side effects. The cetilistat demonstrated the ability to perform as a long-term therapy for constipation, but also for non-opiate medication-related constipation.

Example 3

75-year-old man living in a nursing home with mild dementia complained of painful bowel movements causing an anal fissure with bleeding in his rectum. The cause of his constipation was deemed to be due to a combination of non-opiate medications, dehydration, and a lazy bowel. The patient also complained of abdominal distention and some intermittent abdominal discomfort. The patient was not overweight. A number of common prescription laxatives, including Colace™, senna, and bowel stimulants, caused diarrhea. He had abdominal pain with conventional bowel stimulants. He was then given cetilistat (60 mg orally twice daily with food) which resulted in a bowel movement within 24 to 36 hours that was painless and soft. Over the course of two weeks, the anal fissure had healed and the bleeding had stopped. The patient had regular bowel movements daily and his abdominal bloating and abdominal pain had resolved. The cetilistat resolved the constipation in an acute case and allowed for long-term recovery from a constipation-related complication. Further, it was effective in the treatment of lazy bowel and age-related constipation.

Example 4

A 25-year-old male travelled to Mexico and while there developed acute gastroenteritis. The patient was of average weight (not overweight). He began experiencing vomiting and diarrhea while there. He became dehydrated and eventually was transferred to his home in Canada. The virus had cleared one day after arriving back in Canada. He began eating and drinking but had developed constipation related to post-infection and dehydration. He was given orlistat (120 mg orally once daily with food) by his doctor for one week and this resolved his constipation within 24 hours. Furthermore, the orlistat regulated his bowel movements where they became normal and regular. The improvement was such that after seven days that when he stopped the medication (orlistat), he was able to return to his normal diet. His bowel movements continue to be normal after cessation of the orlistat. The orlistat functioned as a short-term solution for severe constipation related to dehydration, post-gastroenteritis, and gastrointestinal illness.

Example 5

A 45-year-old male of average weight (not overweight) suffered a thoracic spinal injury with transection of the spinal cord resulting in complete paralysis below the third thoracic vertebrae. He went on to develop full paralysis of his muscles below T-3 including the skeletal muscles and smooth muscles of the gut. He developed a paralytic bowel contributing to chronic constipation with overflow and diarrhea. He required regular manual disempaction and Fleet enemas to manage his chronic constipation. The patient was given orlistat (120 mg one pill three times a day with food) by his doctor. This allowed for long-term improvement in bowel formation that was soft and allowed for better function of the bowel movements, bowel peristalsis and more regular passage of stool without interventional care such that it reduced the use of enemas and manual disempaction or enemas. The bowel movements were soft and allowing for more regular, daily movements. This allowed for a significant reduction of therapeutic enemas and manual disempaction. This demonstrates effective use of orlistat for paralytic bowel, but also in constipation requiring interventional methods for care.

Example 6

This is a case of a 35-year-old female who complained of recurring constipation related to her menstrual cycle. She noticed that a few days before the onset of her menstrual cycle and for the week of her menstrual cycle she develops constipation that aggravates her bloating and abdominal pain. She is not overweight. She has tried over-the-counter laxatives and tried some standard prescription laxatives that caused her to feel more bloated. It did not resolve her constipation. Her doctor gave her a prescription of cetilistat (one 60 mg oral pill once a day with food) to be taken one to three days before the onset of her menstruation. In the fourth week of her period, she noticed normalization of her bowel movement and required to take the cetilistat only as needed. Often she only needs to take it three times during her menstrual cycle. During the days where she used the cetilistat, she had good relief of her constipation with regular, soft bowel movements. She found that the cetilistat was effective in her constipation, but also found she only required the cetilistat on a as needed basis, and her bowel movements were normal during the other days of her cycle. Typically, she required the cetilistat 3-7 days per cycle. This demonstrates effectiveness of cetilistat for the treatment of constipation related to dysmennorhea, but may also apply to disease or illness-related constipation. Further, the cetilistat may be used as needed as a medication for constipation.

Example 7

55-year-old male suffering from bowel cancer was given a partial bowel resection with a colostomy and bag. He complained that since his bowel surgery he suffered chronic constipation and hard stools. When he tried the stool softeners, there was some improvement but he still suffered bloating, constipation and abdominal pain. It would sometimes be so hard it could injure and cause bleeding to the ostomy site. His doctor gave him a prescription for orlistat (120 mg orally once daily with food) and this regulated his bowel movements to an average of once a day, softened his stool which allowed for easy passage of his stool through the ostomy site. His problem with bloating greatly improved and he no longer had abdominal pain. This demonstrates the benefits of orlistat for constipation in those who have had colostomies, bowel resection and bowel cancer or neoplasms.

Example 8

A 35-year-old male suffered a head injury in a car accident causing a coma that resulted in the individual being bedridden for three months. During that time, due to lack of movement and deconditioning (being bed-ridden), the patient developed severe constipation requiring Fleet enema and disempaction. He was given a number of prescription laxatives including Colace, senna and bowel stimulants with some improvement but still required regular lower bowel lavage with Fleet enema and manual disempaction. He was given orlistat (initially one 120 mg pill once a day orally with food and then was gradually increased to one 120 mg oral pills three times per day with food for a total of 4 per day) which allowed for softening of his stool, and the formation of regular bowel movements daily. His stools and bowel function gradually became more regular allowing for a reduction of dose of the orlistat (to one 120 mg oral pill twice per day with food) as maintenance. This allowed for cessation of the Fleet enemas and the disempaction.

This demonstrates the use of orlistat for the treatment of constipation related to deconditioning/bedridden, but also a progressive increase in dose to allow for good bowel function and then titration to lower long term effective dosing.

Example 9

This case involves a 35-year-old male with a 15 year history of fibromyalgia. The 35-year-old male reported chronic pain involving the neck, lower back, migraine headaches, abdominal bloating, and constipation with occasional diarrhea. He had been diagnosed with fibromyalgia about 10 years prior, and had chronic abdominal pain, bloating and a formal diagnosis of irritable bowel syndrome. He had had a colonoscopy twice with no abnormalities. Serology, abdominal x-rays, ultrasound of the abdomen and pelvis, were normal. His examination demonstrated the presence of a bloated central abdomen with tenderness that was nonspecific. There were no masses or any signs of acute surgical abdomen. He was taking Lyrica™ 75 mg twice a day, Flexeril™ 10 mg twice a day as needed, Percocet™ 2 twice a day as needed, and Celebrex™ 200 mg once a day. He was given orlistat (120 mg, twice a day as needed to take with food), and he noted that his constipation resolved, his bloating resolved, his occasional diarrhea resolved, and his abdominal pain resolved. His abdominal exam became non-tender, and he had improvement in his overall fibromyalgia. He has continued with the combined medication for over two years with sustained good results.

Example 10

This case involves a non-overweight 29-year-old female with a history of irritable bowel syndrome. The 29-year-old female reported chronic abdominal pain and bloating, minor occasional constipation, minor occasional diarrhea, and lower back pain for the past five years. She was otherwise well. She had 2 colonoscopies, and an ultrasound of the abdomen and pelvis, all of which were normal. She was also taking an oral dose of B12. She was on other medications as well. Her examination demonstrated central bloating, with no masses. There was no rebound or rigidity. She had no enlargement of any organs. She had tenderness globally around her abdomen, tightness of the iliopsoas bilaterally and oblique muscles. Her bowels were tender, and she was chronically uncomfortable and in pain. She was treated with orlistat (120 mg, once or twice a day as needed with food). Over the course of 4 to 6 weeks, she noticed reduced bloating, relaxation of the muscles of her abdomen and lower back, less straining with bowel movements, no episodes of diarrhea, and resolution of her abdominal pain. She felt generally better, and was able to stop taking vitamin B12 because the absorption of her B12 improved with her improved bowel function. Thus, orlistat was useful to treat IBD.

Example 11

This example relates to a 52-year-old female with a 20 year history of irritable bowel syndrome and heartburn. The 52-year-old female reported chronic abdominal pain with bloating, occasional constipation or diarrhea, and epigastric discomfort for over 20 years. She had four colonoscopies over that period of time, and 2 endoscopies of the stomach. The colonoscopies and endoscopies of the stomach showed no pathology. She also had ultrasounds of the abdomen and pelvis which were normal. She had 2 chest x-rays and an MRI of the abdomen, each of which were normal. She was taking Losec™ for her heartburn which was controlled. She was also taking low dose Atenolol™ for her blood pressure as she had developed some minor hypertension. She was otherwise well. Her examination demonstrated a slightly overweight female of about 50 years of age with epigastric tenderness just over the stomach, and generalized bloating of the abdomen. There were no masses, rebound or rigidity. There were no organs that were tender or enlarged. She complained of persistent heartburn despite being on Losec™ and abdominal pain. She was treated with orlistat (120 mg, twice a day each with a meal to be reduced or increased as required up to three per day). She reported that she only required one per day on average and occasionally a second tablet. The results were that she had great improvement of her abdominal pain and heartburn over 4 to 6 weeks. She had great improvement of her bloating. She became more flexible in her abdomen and lower back. She was more comfortable in her walking. Thus, orlistat was useful to treat IBD.

All citations referred to herein are hereby incorporated by reference.

The invention claimed is:

1. A method comprising administering to a patient in need of chronic pain treatment a composition comprising a lipase inhibitor combined with an opioid pain medication to form a single composition, wherein the lipase inhibitor is selected from the group consisting of: orlistat, cetilistat, gt389-255, saponins, platycodin saponins, scabio saponins, sessiloside, chiisanoside, chikusetsusaponins, dioscin, escins, teasaponins, cyclocariosides, polyphenoics, oolong tea polyphenols, polyphenol rich extracts, *nelumbo nucifera* extract, *salacia reticulata* hot water extract, peanut shell extract, *mangifera indica* leaf and steam bark extracts, ct-ii extracts, terpenes, and lipase inhibitors from microbial sources, wherein the composition comprises a dosage of lipase inhibitor of 30-150 mg and a partial or full treatment dosage of the opioid pain medication, wherein said method is to treat chronic pain in a patient and prevents abuse of the opioid pain medication within the single composition.

2. The method of claim 1, wherein the chronic pain results from fibromyalgia or irritable bowel syndrome.

3. The method of claim 1, wherein the lipase inhibitor is selected from the group consisting of: orlistat, cetilistat and lipstatin.

4. The method according to claim 1, wherein the lipase inhibitor is orlistat or cetilistat.

* * * * *